(12) United States Patent
Sweeny et al.

(10) Patent No.: US 9,913,785 B2
(45) Date of Patent: *Mar. 13, 2018

(54) TOPICAL CHICORY EXTRACT SKIN CARE COMPOSITION PROVIDING BROAD SPECTRUM SUNSCREEN

(71) Applicant: Truth Aesthetics LLC, Austin, TX (US)

(72) Inventors: Sara Sweeny, Austin, TX (US); Fred H. Khoury, Chatsworth, CA (US)

(73) Assignee: Truth Aesthetics LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/169,595

(22) Filed: May 31, 2016

(65) Prior Publication Data

US 2017/0027829 A1    Feb. 2, 2017

Related U.S. Application Data

(63) Continuation of application No. 14/814,126, filed on Jul. 30, 2015, now Pat. No. 9,351,911.

(51) Int. Cl.
| | |
|---|---|
| *A61Q 19/04* | (2006.01) |
| *A61K 8/29* | (2006.01) |
| *A61Q 17/04* | (2006.01) |
| *A61K 8/97* | (2017.01) |
| *A61K 8/37* | (2006.01) |
| *A61K 8/92* | (2006.01) |
| *A61K 8/49* | (2006.01) |
| *A61Q 19/08* | (2006.01) |

(52) U.S. Cl.
CPC ............... *A61K 8/29* (2013.01); *A61K 8/37* (2013.01); *A61K 8/375* (2013.01); *A61K 8/498* (2013.01); *A61K 8/922* (2013.01); *A61K 8/97* (2013.01); *A61Q 17/04* (2013.01); *A61K 2800/522* (2013.01); *A61K 2800/596* (2013.01); *A61Q 19/04* (2013.01); *A61Q 19/08* (2013.01)

(58) Field of Classification Search
CPC .................. A61Q 17/04; A61Q 91/04
See application file for complete search history.

(56) References Cited

U.S. PATENT DOCUMENTS

| | | |
|---|---|---|
| 6,071,541 A | 6/2000 | Murad |
| 6,338,855 B1 | 1/2002 | Albacarys et al. |
| 6,375,992 B1 | 4/2002 | Blumenstein-Stahl et al. |
| 6,630,163 B1 | 10/2003 | Murad |
| 7,320,797 B2 | 1/2008 | Gupta |
| 8,071,555 B2 | 12/2011 | Zhang et al. |
| 8,211,873 B2 | 7/2012 | Gupta et al. |
| 8,586,730 B2 | 11/2013 | Peter et al. |
| 9,351,911 B1 * | 5/2016 | Sweeney ............... A61K 8/922 |
| 2008/0107679 A1 | 5/2008 | Dilallo et al. |
| 2010/0047193 A1 | 2/2010 | Fishman |
| 2011/0229538 A1 | 9/2011 | Matravers et al. |
| 2013/0028853 A1 | 1/2013 | Nurse et al. |
| 2013/0039961 A1 | 2/2013 | Gonzales et al. |
| 2013/0172291 A1 | 7/2013 | Peter et al. |
| 2013/0336903 A1 | 12/2013 | Fernandez Prieto et al. |
| 2013/0336909 A1 | 12/2013 | Garaud et al. |

OTHER PUBLICATIONS

International Search Report for PCT/US16/29381 dated Jun. 20, 2016.

* cited by examiner

*Primary Examiner* — Carlos Azpuru
(74) *Attorney, Agent, or Firm* — Rutan & Tucker LLP; Hani Z. Sayed

(57) ABSTRACT

A topical skin care composition providing broad spectrum protection from harmful rays of the sun containing a combination of ultrafine titanium dioxide, a moisturizing saccharide complex, an anti-oxidant complex, a chicory extract rich in oligofructosans, and various other components for topical application to the skin. The composition provides protection from the sun's rays and promotes rejuvenation of the skin and inhibits damage to skin caused by dehydration and environmental factors and promotes skin health by supplying vitamin D to the skin to make up for the loss of natural vitamin D production caused by blocking the sun's rays.

21 Claims, No Drawings

TOPICAL CHICORY EXTRACT SKIN CARE COMPOSITION PROVIDING BROAD SPECTRUM SUNSCREEN

BACKGROUND

This invention is related to a topical skin care composition as well as methods of using same. More specifically, the invention relates to a topical skin care composition for use during the day to protect against environmental hazards, pollutants and thermal and infra-red radiation.

The skin ages as a natural consequence of exposure to various environmental factors. Among these factors is exposure to air pollutants, as well as thermal and infra-red radiation. It is reported that over 85% of the visible signs of aging are due to the negative effect of these factors on the skin. Other factors that may play a part in the aging process of the skin include, for example, weathering of the skin, exposure to cigarette smoke and Ultra-Violet (UV) radiation.

Sunscreens having a high sun protection factor (SPF) do protect the skin from damage caused by exposure to solar radiation, particularly damage caused by the UV components, such as UVA, which refers to light having a wavelength of 320-400 nanometers, and UVB, which refers to light having a wavelength of 280-320 nanometers. While use of high SPF sunscreens is beneficial in protecting the skin, one consequence of their use is that the production of vitamin D in the skin is reduced. As is well known in the art, vitamin D is necessary for cell division and differentiation. Thus, reduced levels of vitamin D can result in increased aging of the skin.

Most conventional cosmetic products merely temporarily mask the signs of aging, and do little to adequately protect the skin's collagen and elastin network from the effects of the environmental factors listed above. What has been needed, and heretofore unavailable, is a topically applied skin care formulation for use to shield the skin from damage caused by exposure to environmental factors, such as damage caused by exposure to the rays of the sun during the day. Such a formulation should also provide a source of vitamin D for use by the skin cells, since the production of vitamin D by skin cells is reduced when a high SPF sunscreen is used to block the sun's rays. The present invention satisfies these and other needs.

SUMMARY OF THE INVENTION

In its most general aspect, the present invention includes a topical skin care composition containing ultrafine titanium dioxide, a moisturizing saccharide complex, an anti-oxidant complex, and a chicory extract rich in oligofructosans, and various other components forming an acceptable cosmetic carrier, pH adjusters, thickeners, and the like known to those skilled in the art. The combination provides protection from the sun's rays and promotes rejuvenation of the skin and inhibits damage to skin caused by dehydration and environmental factors. The composition may be used in conjunction with the application of other topical skin care products. As a result, the composition provides surprising performance benefits in not only protecting the skin from the harmful effects of the sun, but also promotes skin health by supplying vitamin D to the skin to make up for the loss of natural vitamin D production caused by blocking the sun's rays. Use of the composition assists in firming and hydrating the skin and promoting a younger appearance.

In another aspect, the various components described above are blended with a cosmetically acceptable carrier which may include purified water, oils, alcohols, glycols, and combinations thereof.

In yet another aspect, the topical skin care composition may further comprise additional ingredients such as penetration enhancers, humectants, lubricants, pharmaceutically active agents, color, fragrance, preservatives, antioxidants, chelators, neutralizers, amino acids, anti-inflammatory agents, anti-irritants, anti-tack agents, astringents, binders, catalysts, stabilizers, emollients, emulsifiers, surfactants, cell-signaling agents, essential oils, plant/botanical extracts, conditioners, film formers, gelling agents, foaming agents, exfoliants, vitamins, minerals, pH adjusters, proteins, peptides, tactile enhancers, saccharides, solvents or any combination thereof.

In still another aspect, the topical skin care composition may be formulated as a cream, lotion, serum, facial cleanser, toner, eye cream, sunscreen, stick, spray, impregnated personal care device, impregnated towelette, gel, fluid/liquid, soap, oil, butter, peel, scrub, mask, concentrate, or any other form known in the art.

In another aspect, the present invention includes a topical skin care composition comprising: a topical skin care composition comprising: (a) water; (b) acrylates and alkyl acrylate crosspolymer; (c) a xanthan gum; (d) propanediol; (e) glycerin; (f) a source of moisturizing saccharide complex; (g) a *cichorium intybus* (chicory) root extract, phenoxyethanol, and ethylhexylglycerin complex; (h) a phenethyl alcohol and ethyhexylglycerin complex; (j) a source of stearoxymethicone/dimethicone copolymer; (k) a source of caprylyl-caprylate/caprate; (l) a source of diisopropyl dimer dilinoleate; (m) a source of butyloctyl salicylate; (n) a source of coconut alkanes and coco-caprylate/caprate; (o) a source of *simmondsia chinensis* seed oil; (p) a complex of *oryza satia* (rice) bran extract, *rosmarinus officinalis* (rosemary) leaf extract, *heliantus annuus* (sunflower) seed oil and tocopherol; (q) a source of lauryl glucoside; (r) a source of polyhdroxystearic acid; (s) a complex of mica and silica; (t) a complex of mica and iron oxide; and (u) a source of titanium dioxide, which may be combined with other constituents, such as C12-15 alkyl benzoate, cyclopentasiloxane, stearic acid, polyhydroxystearic acid and alumina; and (v) a source of aminomethyl propanol.

In a further aspect, the invention includes a method of treating skin comprising applying a topical skin care composition containing ultrafine titanium dioxide, a moisturizing saccharide complex, an anti-oxidant complex, and a chicory extract rich in oligofructosans, and various other components forming an acceptable cosmetic carrier, pH adjusters, thickeners, and the like known to those skilled in the art.

In still another aspect, a topical skin care composition in accordance with the principles of the invention is applied to the skin, often the face, which may have, for example, but is not limited to, wrinkles, fine lines, uneven tone, loss of firmness, surface roughness, dark circles, under-eye puffiness, sun damage, redness, dryness, irritation, enlarged ports and combinations of all or some of the above. Alternatively, the topical skin care composition may be applied to the skin to prevent the occurrence of the various problems described above.

In yet another aspect, the topical skin care composition in accordance with the principles of the invention is applied to skin in an amount and for a period of time sufficient to treat the skin for the condition treated. In one alternative aspect, the topical skin care composition is applied at least once a day. In another alternative aspect, the topical skin care composition is applied more than once a day.

In still another aspect, a user of the topical skin care composition in accordance with the principles of the invention applies a thin, even layer of the topical skin care composition of the present invention to the face, neck, or other portions of the body. The topical skin care composition is then gently massaged into the skin.

In another aspect, the present invention includes a topical skin care composition comprising: (a) ultrafine titanium dioxide; (b) a source of moisturizing saccharide complex; (c) an antioxidant complex; (d) a chicory root extract; and (e) a cosmetically acceptable carrier.

In one aspect, the titanium dioxide is present in the amount of 10.44% by weight to 12.76% by weight. In another aspect, the titanium dioxide is present in the amount of 20% to 30% by weight.

In yet another aspect, the source of moisturizing saccharide complex is an apple extract. In one alternative aspect, the source of moisturizing saccharide complex is present in the amount of 0.5% to 10.0% by weight.

In still another aspect, the source of anti-oxidant components is a complex of rice bran extract, rosemary leaf extract, sunflower seed oil and tocopherol. In one alternative aspect, the source of anti-oxidant components is present in the amount of 0.1% and 2.0% by weight.

In yet another aspect, the source of the chicory root extract is present in the amount of 1.5% to 3.3% by weight.

In a further aspect, the topical skin care composition of the present invention further comprises one or more emollient compounds. In one alternative aspect, at least one of the one or more emollient compounds is *simmondsia chinensis* oil. In another alternative aspect, the at least one of the one or more emollient compounds is caprylic/capric triglyceride. In still another alternative aspect, the one of the one or more emollient compounds is capryloyl-caprylate/caprate.

In another aspect, the topical skin care composition of the present invention further comprises one or more humectant compounds.

In still another further aspect, the topical skin care composition of the present invention further comprises one or more SPF stabilizing compounds. In one alternative aspect, the SPF stabilizing compound is butyloctyl salicylate. In another alternative aspect, the SPF stabilizing compound includes mica. In still another alternative aspect, the SPF stabilizing compound includes silica.

In another further aspect, the topical skin care composition of the present invention further comprises a pH modifier. In still another further aspect, the topical skin care composition of the present invention further comprises a preservative compound. In yet another further aspect, the topical skin care composition of the present invention further comprises a viscosity modifier.

In another aspect, the present invention includes a method of treating the skin comprising applying to the outer surface of the skin a topical skin care composition comprising: (a) ultrafine titanium dioxide; (b) a source of moisturizing saccharide complex; (c) an antioxidant complex; (d) a chicory root extract; and (e) a cosmetically acceptable carrier.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

As used herein, the phrases "selected from the group consisting of," "chosen from," and the like include mixtures of the specified materials. Terms such as "contains" and the like are meant to include "including at least" unless otherwise specifically noted.

Where a numerical limit or range is stated, the endpoints are included. Also, all values and subranges within a numerical limit or range are specifically included as if explicitly written out.

The various embodiments and compositions described herein are typically used by persons desiring to protect their skin from harmful environmental factors, or to repair skin that has been previously damaged by such factors. For example, persons using those compositions may seek to prevent damage to the skin caused by lack of hydration, exposure to the sun, inflammation or infrared radiation. Benefits of using the compositions of the present invention include retaining and/or restoring and/or improving physical and mechanical properties of the skin which includes smoothness, taughtness, resiliency and radiance.

The present invention is directed to a topical skin care composition containing ultrafine titanium dioxide, a moisturizing saccharide complex, an anti-oxidant complex, and a chicory extract rich in oligofructosans, and various other components forming an acceptable cosmetic carrier, pH adjusters, thickeners, and the like known to those skilled in the art. The combination provides protection from the sun's rays and promotes rejuvenation of the skin and inhabits damage to skin caused by dehydration and environmental factors. The composition may be used in conjunction with the application of other topical skin care products. As a result, the composition provides surprising performance benefits in not only protecting the skin from the harmful effects of the sun, but also promotes skin health by supplying vitamin D to the skin to make up for the loss of natural vitamin D production caused by blocking the sun's rays. Use of the composition assists in firming and hydrating the skin and promoting a younger appearance.

The ultrafine titanium dioxide used in the compositions of the present invention may be obtained from commercial sources. Ultrafine titanium dioxide has been found to provide protection from solar irradiation in both the UVA (320-400 nm) spectrum and the UVA (280-320 nm) spectrum. One source for ultrafine titanium dioxide is UV CUT TiO2-55-AC sold by Grant Industries, Inc. The compound available from Grant Industries, Inc. includes C12-15 alkyl benzoate, cyclopentasiloxane, stearic acid, polyhroxystearic acid and alumina.

According to one embodiment or composition of the invention, the ultrafine titanium dioxide is present in an amount ranging from 20% to 30% by weight of the topical skin care composition, and preferably from about 22.5% to 27.5% by weight of the topical skin care composition, and most preferably in an amount ranging from 24.0% to 26% by weight of the topical skin care composition.

The moisturizing saccharide complex used in the compositions of the present invention may be obtained from commercial sources. In one embodiment, the moisturizing saccharide complex is an extract from dried apples. The moisturizing saccharide complex has been found to moisturize and smooth skin texture. One source for such an extract from dried apples is Botanimoist AMS, which contains *Pyrus Malus* (Apple) extract and glycerin, sold by Botanigenics, Inc.

According to one embodiment or composition of the invention, the moisturizing saccharide complex is present in an amount ranging from 0.5% to 10.0% by weight of the topical skin care composition, and preferably from about 0.5% to 5.0% by weight of the topical skin care composition, and most preferably in an amount ranging from 0.9% to 1.1% by weight of the topical skin care composition.

The anti-oxidant complex used in the compositions of the present invention may be obtained from commercial sources. In one embodiment, the anti-oxidant complex is composed of rice extract, rosemary extract, sunflower extract and natural tocopherols and may be obtained from commercial sources. This anti-oxidant complex has been found to protect natural oils of the skin from oxidative degradation. One source for such an anti-oxidant complex is Bottanessential RRST sold by Botanigenics (USA).

According to one embodiment or composition of the invention, the anti-oxidant complex is present in an amount ranging from 0.1% to 2.0% by weight of the topical skin care composition, and preferably from about 0.1% to 1.1% by weight of the topical skin care composition, and most preferably in an amount ranging from 0.1% to 1.0% by weight of the topical skin care composition.

The chicory extract complex used in the compositions of the present invention is rich in oligofructosans and provides a vitamin D-like function in enabling the skin to recover an optimum epidermal barrier without exposure to UV irradiation. One source for such chicory extract is Vederine® sold by Silab. The product available from Silab includes an extract of *cichorium intybus* root, phenoxyethanol, and ethylhexlyglycerin.

According to one embodiment or composition of the invention, the chicory extract complex is present in an amount ranging from 0.5% to 3.3% by weight of the topical skin care composition, and preferably from about 0.5% to 3.0% by weight of the topical skin care composition, and most preferably in an amount ranging from 2.0% to 3.0% by weight of the topical skin care composition.

Other components may also be included in the compositions of various embodiments of the present invention. For example, purified water may be used as a diluent. Carpobol Ultrez 20, available from Lubrazol, which is a mixture of acrylates/C10-30 alkyl acrylate crosspolmer, may be used as a thickener and carrier. Xanthan gum, such as Kelrol CG-RD, sold by CP Kelco, may be used to adjust viscosity. Aminomethyl propanol, such as AMP Ultra PC 2000, sold by Angus, may be used as a pH modifier. Propanediol and glycerin may be used as humectants. A blend of phenethyl alcohol and ethlyhexylglycerin, such as Sensiva PA 20, sold by Schulke, Inc., may be used as a preservative. Stearoxymethicone/Dimethicone copolymer, such as Gransil VX-402, sold by Grant Industries, Inc. may be used as a thickener or film former. Caprylyl-caprylate/caprate, such as Cetiol RLF, available from BASF, diisopropyl dimer dilinoleate, such as Schercemol DID, sold by Lubrizol Corporation, caprylic/capric triglyceride, available from local sources, and *simmondsia chinesis* seed oil, such as Golden Jojoba Oil, sold by Jedwards, may be used as emollients.

Additionally, coconut alkanes and coco-caprylate/caprate, such as Vegelight 1214LC, sold by Grant Industries, Inc., may be used as a solvent. Butyloctyl salicylate, such as Hallbright BHB, sold by Hallstar Co., and mica and/or silica, such as NS Boost, sold by Next Step Laboratories, may be used as SPF stabilizers. Lauryl glucoside, such as PLANTACARE 1200 UP, sold by BASF, may be used as a surfactant; and polyhydroxystearic acid, such as Pelemol PHS-8, sold by Phoenix Chemical, may be used as a dispersant. A combination of mica and iron oxide, such as Super Soft Bronze, sold by Sudarshan Chemical Industries (India) may also be used as a pigment.

The invention is now more fully illustrated using the following example, which is not to be understood as limiting the invention to the embodiments described.

EXAMPLE 1

A topical cream for day use to provide a broad spectrum sunscreen was prepared using the ingredients set forth in Table 1 below.

TABLE 1

| | Ingredient | % w/w |
|---|---|---|
| 1 | Water (USP) | 33.175 |
| 2 | Acrylates/C10-30 Alkyl Acrylate Crosspolymer | 0.150 |
| 3 | Xanthan Gum | 0.075 |
| 4. | Propanediol | 3.000 |
| 5 | Glycerin | 8.000 |
| 6 | Pyrus Malus (Apple) Fruit Extract Glycerin | 1.000 |
| 7 | Cichorium Intybus (Chicory) Root Extract Phenoxyethanol Ethylhexylglycerin | 3.000 |
| 8 | Phenethyl Alcohol Ethylhexylgycerin | 1.000 |
| 9 | Stearoxymethicone/Dimethicone Copolymer | 1.750 |
| 10 | Caprylyl-Caprylate/Caprate | 1.000 |
| 11 | Diisopropyl Dimer Dilinoleate | 1.000 |
| 12 | Butyloctyl Salicylate | 5.000 |
| 13 | Coconut Alkanes Coco-Caprylate/Caprate | 5.000 |
| 14 | Caprylic/Capric Triglyceride | 4.000 |
| 15 | Simmondsia Chinensis Seed Oil | 1.000 |
| 16 | Oryza Sative (Rice) Bran Extract Rosmarinus Officinalis (Rosemary) Leaf Extract Heliantus Annuus (Sunflower) Seed Oil Tocopherol | 1.000 |
| 17 | Lauryl Glucoside | 1.750 |
| 18 | Polyhydroxystearic Acid | 0.500 |
| 19 | Mica Silica | 3.000 |
| 20 | Mica Iron Oxide (Cl 77491) | 0.500 |
| 21 | Titanium Dioxide C12-15 Alkyl Benzoate Cyclopentasiloxane Stearic Acid/Polydroxystearic Acid Alumina | 25.000 |
| 22 | Aminomethyl Propanol | 0.100 |

The topical cream for day use to provide a broad spectrum sunscreen was prepared by combining a Phase A containing ingredients 1 through 8 in one mixing tank and a Phase B containing ingredients 9 through 19 in another mixing tank and heating both tanks to 70 degrees centigrade. Phase A was then added to Phase B and mixed for ten minutes. The components of ingredient 21 were premixed and then added to ingredient 20 to form a Phase C. Phase C was then added to the mixture of Phase A and Phase B and homogenized for ten minutes at 3000-4000 RPM and then prop mixed and cooled to 30 degrees centigrade. Ingredient 22 is added to the mixture and mixed for 20 minutes. All processing tanks and other equipment were sanitized before use.

The resulting topical broad spectrum sunscreen day cream is a light pink lotion. The pH at 25 degrees centigrade was 7.25-7.75, the viscosity was between 7500-20,000 cPs, as measured using a Brookfield Viscometer LVT. Specific gravity at 25 degrees centigrade was 1.097-1.137.

In a second example, a topical cream for day use to provide a broad spectrum sunscreen was prepared using the ingredients set forth in Table 2 below.

TABLE 2

| | Ingredient | % w/w |
|---|---|---|
| 1 | Water (USP) | 30.768 |
| 2 | Acrylates/C10-30 Alkyl Acrylate Crosspolymer | 0.300 |
| 3 | Xanthan Gum | 0.150 |
| 4. | Propanediol | 5.000 |
| 5 | Glycerin | 2.000 |
| 6 | Pyrus Malus (Apple) Fruit Extract<br>Glycerin | 5.000 |
| 7 | Cichorium Intybus (Chicory) Root Extract<br>Phenoxyethanol<br>Ethylhexylglycerin | 3.000 |
| 8 | Phenethyl Alcohol<br>Ethylhexylgycerin | 1.000 |
| 9 | Stearoxymethicone/Dimethicone Copolymer | 3.000 |
| 10 | Caprylyl-Caprylate/Caprate | 2.500 |
| 11 | Diisopropyl Dimer Dilinoleate | 2.000 |
| 12 | Butyloctyl Salicylate | 5.000 |
| 13 | Coconut Alkanes<br>Coco-Caprylate/Caprate | 5.000 |
| 14 | Caprylic/Capric Triglyceride | 2.000 |
| 15 | Simmondsia Chinensis Seed Oil | 2.000 |
| 16 | Oryza Sative (Rice) Bran Extract<br>Rosmarinus Officinalis (Rosemary) Leaf Extract<br>Heliantus Annuus (Sunflower) Seed Oil<br>Tocopherol | 1.000 |
| 17 | Lauryl Glucoside | 0.500 |
| 18 | Polyhydroxystearic Acid | 1.000 |
| 19 | Mica<br>Silica | 1.500 |
| 20 | Mica<br>Iron Oxide (Cl 77491) | 0.432 |
| 21 | Titanium Dioxide<br>C12-15 Alkyl Benzoate<br>Cyclopentasiloxane<br>Stearic Acid/Polydroxystearic Acid<br>Alumina | 26.500 |
| 22 | Aminomethyl Propanol | 0.350 |

The topical cream for day use to provide a broad spectrum sunscreen was prepared by combining a Phase A containing ingredients 1 through 8 in one mixing tank and a Phase B containing ingredients 9 through 19 in another mixing tank and heating both tanks to 70 degrees centigrade. Phase A was then added to Phase B and mixed for ten minutes. The components of ingredient 21 were premixed and then added to ingredient 20 to form a Phase C. Phase C was then added to the mixture of Phase A and Phase B and homogenized for ten minutes at 3000-4000 RPM and then prop mixed and cooled to 30 degrees centigrade. Ingredient 22 is added to mixture and mixed for 20 minutes. All processing tanks and other equipment were sanitized before use.

The resulting topical broad spectrum sunscreen day cream is a light pink lotion. The pH at 25 degrees centigrade was between 7.25-7.75, the viscosity was between 7,500-20,000 cps as measured using a Brookfield Viscometer LVT. Specific gravity at 25 degrees centigrade was between 1.097-1.137.

The examples presented above provide a process for making and using the various embodiments of the invention to enable a person skilled in the art to make and use the same. It will be understood that the various examples may be used to protect a user's face and other skin areas from the harmful effects of various environmental factors, such as exposure to the rays of the sun. It will also be understood that the various embodiments of the invention may be used in concert with other topical liquids, creams, sprays and the like without departing from the intended scope of the invention.

In another embodiment, the invention includes a method of treating skin comprising applying a topical skin care composition such as is described above to the skin. Typically, the topical skin care composition is applied to the skin, often the face, which may, for example, but not limited to, have wrinkles, fine lines, uneven tone, loss of firmness, surface roughness, dark circles, under-eye puffiness, sun damage, redness, dryness, irritation, enlarged ports and combinations of all or some of the above. Alternatively, the topical skin care composition may be applied to the skin to prevent the occurrence of the various problems described above.

The novel compositions of the present invention are used by subjects desiring to obtain the benefits noted above, including the hydration of their skin, increasing the skins resiliency and radiance, protecting against harmful UV radiation from the sun's rays, and providing protection against inflammation-related signs of aging, such as fine lines and wrinkles. Use of the various compositions of the invention may decrease the size of skin pores, even out the tone of the skin, and improve the texture of the skin.

Typically, a person using the compositions of the various embodiments of the present invention apply them to the their skin in amounts that obtain one or more of the noted benefits. For example, the compositions of the invention may be applied to a skin area so as to improve the texture of the skin, reduce pore size, or hydrate dry skin. Alternatively, the composition may be applied as a sunscreen to prevent damage to the skin caused the sun's rays.

The amount used is typically sufficient to obtain coverage of a desired area of the skin, such as the face, with a single application. The compositions may also be used over the course of a period of time, with the amount of the composition used including the amount used during repeated applications. For example, the compositions may be applied to a desired area of the skin on a daily basis, either once a day or several times per day, over the course of days, weeks, months or any time period desired by the user. The various compositions of the invention are typically considered to be light-weight, easily absorbed and layer cleanly under or over makeup or other substances applied to the skin without pilling or feeling heavy.

The topical skin care compositions of the various embodiments of the present invention may be formulated to be used on an "as needed" basis, or they may be formulated for application at specific times of the day, or multiple times during the time the user is awake. They may also be formulated for use on an every other day, weekly, monthly or other basis. The compositions may also be formulated for application by the fingers of the user, or they may be formulated for application by some application means, such as, for example, a soft pad or other applicator well known in the art. The compositions may also be used as part of a skin treatment regimen, and may also be used in conjunction with other skin creams and makeup.

In one embodiment, a user of a topical skin care composition in accordance with the present invention applies a thin, even layer of the skin care composition in accordance with the present invention to the face, neck, or other portions of the body. The topical skin care composition is then gently massaged into the skin. This process may be performed as needed during the day to provide a sunscreen for the skin.

While particular embodiments of the present invention have been described, it is understood that various different modifications within the scope and spirit of the invention are possible. The invention is limited only by the scope of the appended claims.

We claim:

1. A topical skin care composition comprising:
   an ultrafine titanium dioxide to provide protection from solar irradiation;
   a moisturizing saccharide complex to moisturize and smooth skin texture;
   an anti-oxidant complex to protect natural oils of the skin from oxidative degradation;
   a chicory extract complex to enable the skin to recover an optimum epidermal barrier without exposure to UV irradiation; and
   one or more components to form a cosmetically acceptable carrier.

2. The composition of claim 1, wherein any one or more of the ultrafine titanium dioxide, the moisturizing saccharide complex, the anti-oxidant complex, and the chicory extract complex may be obtained from commercial sources.

3. The composition of claim 1, wherein the ultrafine titanium dioxide provides protection from solar irradiation in at least the UVA (320-400 nm) spectrum and the UVA (280-320 nm) spectrum.

4. The composition of claim 1, wherein the ultrafine titanium dioxide comprises a compound that includes any one or more of C12-15 alkyl benzoate, cyclopentasiloxane, stearic acid, polyhroxystearic acid and alumina.

5. The composition of claim 1, wherein the moisturizing saccharide complex is comprised of an extract from dried apples.

6. The composition of claim 5, wherein the moisturizing saccharide complex is comprised of at least *Pyrus Malus* extract and glycerin.

7. The composition of claim 1, wherein the anti-oxidant complex is comprised of any one or more of rice extract, rosemary extract, sunflower extract and natural tocopherols.

8. The composition of claim 1, wherein the chicory extract complex is comprised of oligofructosans so as to provide a vitamin D-like function in enabling the skin to develop an epidermal barrier in absence of exposure to UV irradiation.

9. The composition of claim 1, wherein the chicory extract complex is comprised of any one or more of an extract of *cichorium intybus* root, phenoxyethanol, and ethylhexlyglycerin.

10. The composition of claim 1, wherein the ultrafine titanium dioxide comprises an amount ranging from 24.0% to 26% by weight of the composition, the moisturizing saccharide complex comprises an amount ranging from 0.9% to 1.1% by weight of the composition, the anti-oxidant complex comprises an amount ranging from 0.1% to 1.0% by weight of the composition, and the chicory extract complex comprises an amount ranging from 2.0% to 3.0% by weight of the composition.

11. The composition of claim 1, wherein the ultrafine titanium dioxide comprises a portion ranging from 10.44% to 12.76% by weight of the topical skin care composition, the moisturizing saccharide complex comprises a portion ranging from 0.5% to 10.0% by weight of the topical skin care composition, the anti-oxidant complex comprises a portion ranging from 0.1% to 2.0% by weight of the topical skin care composition, and the chicory extract complex comprises a portion ranging from 1.5% to 3.3% by weight of the topical skin care composition.

12. The composition of claim 1, wherein the one or more components are comprised of any one or more of caprylyl-caprylate/caprate, diisopropyl dimer dilinoleate, caprylic/capric triglyceride, and *simmondsia chinesis* seed oil to operate as emollients.

13. The composition of claim 1, wherein the one or more components are comprised of any one or more of butyloctyl salicylate, mica, and silica to operate as SPF stabilizers.

14. The composition of claim 1, wherein the one or more components are comprised of a mixture of acrylates/C10-30 alkyl acrylate crosspolmer to operate as a thickener and carrier.

15. The composition of claim 1, wherein the one or more components are comprised of aminomethyl propanol to operate as a pH modifier.

16. The composition of claim 1, wherein the one or more components are comprised of any one or more of propanediol and glycerin to operate as humectants.

17. The composition of claim 1, wherein the one or more components are comprised of a blend of phenethyl alcohol and ethlyhexylglycerin to operate as a preservative.

18. The composition of claim 1, wherein the one or more components are comprised of stearoxymethicone/dimethicone copolymer to operate as a thickener.

19. The composition of claim 1, wherein the one or more components are comprised of coconut alkanes and coco-caprylate/caprate to operate as a solvent.

20. The composition of claim 1, wherein the one or more components are comprised of lauryl glucoside to operate as a surfactant.

21. The composition of claim 1, wherein the one or more components are comprised of polyhydroxystearic acid to operate as a dispersant.

* * * * *